United States Patent
Christenson et al.

(12) 
(10) Patent No.: US 7,434,312 B2
(45) Date of Patent: Oct. 14, 2008

(54) METHOD FOR MANUFACTURING AN IMPLANTABLE DRUG DELIVERY DEVICE WITH PERISTALTIC PUMP HAVING A RETRACTABLE ROLLER

(75) Inventors: Steven R. Christenson, Coon Rapids, MN (US); Reginald D. Robinson, Plymouth, MN (US); Kenneth T. Heruth, Edina, MN (US); James M. Haase, Maplewood, MN (US); Mandred K. Luedi, Koniz (CH)

(73) Assignee: Medtronic, Inc., Minneapolis, MN (US)

( * ) Notice: Subject to any disclaimer, the term of this patent is extended or adjusted under 35 U.S.C. 154(b) by 845 days.

(21) Appl. No.: 10/826,088

(22) Filed: Apr. 16, 2004

(65) Prior Publication Data

US 2004/0199118 A1 Oct. 7, 2004

Related U.S. Application Data

(62) Division of application No. 09/834,874, filed on Apr. 13, 2001, now Pat. No. 6,743,204.

(51) Int. Cl.
*B23P 15/00* (2006.01)
*A61M 1/00* (2006.01)

(52) U.S. Cl. ............... 29/888.022; 604/151; 417/477.7

(58) Field of Classification Search ........... 29/888.022; 604/151, 153, 131; 414/477.7, 477.3, 477.1, 414/474, 476, 423.6; 417/477.7, 477.3, 477.1, 417/474, 476, 423.6

See application file for complete search history.

(56) References Cited

U.S. PATENT DOCUMENTS

| | | |
|---|---|---|
| 2,804,023 A | 8/1957 | Lee |
| 2,920,578 A | 1/1960 | Schaurte |
| 3,644,068 A | 2/1972 | Lepak |
| 3,822,948 A | 7/1974 | Handl |
| 3,885,894 A | 5/1975 | Sikes |
| 3,918,453 A | 11/1975 | Leonard |

(Continued)

FOREIGN PATENT DOCUMENTS

DE 24 52 771 A1 5/1976

(Continued)

OTHER PUBLICATIONS

OEM Custom Pump Catalog, Watson-Marlow Bredel OEM Catalog, Publication date Mar. 2000.

(Continued)

*Primary Examiner*—David P. Bryant
*Assistant Examiner*—Sarang Afzali
(74) *Attorney, Agent, or Firm*—Banner & Witcoff, Ltd.

(57) ABSTRACT

An implantable drug infusion device includes a pump tube for holding a liquid to be pumped. A race is configured to support the pump tube. A roller assembly is configured to compress the tube against the race at one or more points along the path, and the roller assembly includes at least one roller and a hub. A drive assembly drives the roller assembly relative to the tube along the path so as to move the liquid through the tube. A retracting roller is operably connected to the hub and/or one or more adjacent rollers to permit retraction of the roller during installation of the pump tube between the roller and the race.

18 Claims, 15 Drawing Sheets

U.S. PATENT DOCUMENTS

| | | | |
|---|---|---|---|
| 3,927,955 | A | 12/1975 | Spinosa et al. |
| 3,960,466 | A | 6/1976 | Taylor |
| 3,963,023 | A | 6/1976 | Hankinson |
| 3,990,444 | A | 11/1976 | Vial |
| 4,012,177 | A | 3/1977 | Yakich |
| 4,013,074 | A | 3/1977 | Siposs |
| 4,142,845 | A * | 3/1979 | Lepp et al. ............... 417/477.8 |
| 4,256,437 | A | 3/1981 | Brown |
| 4,363,609 | A | 12/1982 | Cosentino et al. |
| 4,525,164 | A | 6/1985 | Loeb et al. |
| 4,545,744 | A | 10/1985 | Weber et al. |
| 4,564,342 | A | 1/1986 | Weber et al. |
| 4,576,556 | A | 3/1986 | Thompson |
| 4,650,471 | A | 3/1987 | Tamari |
| 4,685,902 | A | 8/1987 | Edwards et al. |
| 4,692,147 | A | 9/1987 | Duggan |
| 4,950,136 | A | 8/1990 | Haas et al. |
| 5,064,358 | A | 11/1991 | Calari |
| 5,082,429 | A | 1/1992 | Soderquist et al. |
| 5,083,908 | A | 1/1992 | Gagnebin et al. |
| 5,096,393 | A | 3/1992 | Van Steenderen et al. |
| 5,125,801 | A | 6/1992 | Nabity et al. |
| 5,213,483 | A | 5/1993 | Flaherty et al. |
| 5,215,450 | A | 6/1993 | Tamari |
| 5,266,013 | A | 11/1993 | Aubert et al. |
| 5,405,614 | A | 4/1995 | D'Angelo et al. |
| 5,576,503 | A | 11/1996 | Nabity et al. |
| 5,578,001 | A | 11/1996 | Shah |
| 5,741,125 | A | 4/1998 | Neftel et al. |
| 5,752,930 | A | 5/1998 | Rise et al. |
| 5,840,069 | A | 11/1998 | Robinson |
| 5,915,932 | A | 6/1999 | Nabity et al. |
| 6,036,459 | A | 3/2000 | Robinson |
| 6,626,867 | B1 | 9/2003 | Christenson et al. |
| 6,645,176 | B1 | 11/2003 | Christenson et al. |
| 6,745,204 | B1 | 6/2004 | Hogue et al. |

FOREIGN PATENT DOCUMENTS

| | | |
|---|---|---|
| DE | 3737023 | 7/1988 |
| DE | 101 19 391 | 11/2001 |
| EP | 0 174 535 A1 | 3/1986 |
| EP | 0 239 255 | 9/1987 |
| EP | 0 320 441 | 6/1989 |
| EP | 0 344 640 A1 | 12/1989 |
| EP | 0 547 550 A1 | 6/1993 |
| FR | 2 021 524 | 7/1970 |
| FR | 2 644 853 A1 | 9/1990 |
| FR | 2 719 873 A1 | 11/1995 |
| FR | 2 808 203 | 11/2001 |
| GB | 681 | 0/1902 |
| SU | 547550 | 2/1977 |

OTHER PUBLICATIONS

Sta-Pure Peristaltic Pump Tube, Watson-Marlow Bredel Pump Brochure.

OEM: Peristaltic Pumps for Engineers, Watson-Marlow Limited Pump Brochure.

* cited by examiner

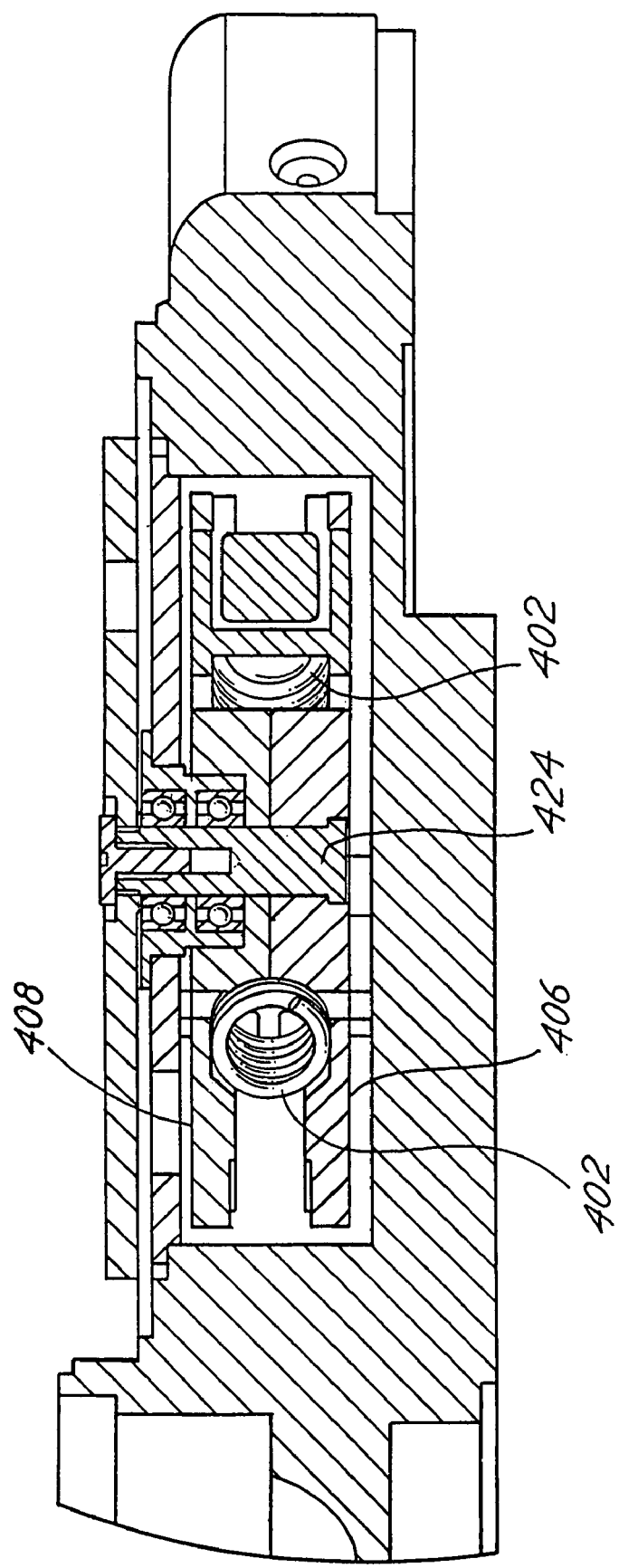

METHOD FOR MANUFACTURING AN IMPLANTABLE DRUG DELIVERY DEVICE WITH PERISTALTIC PUMP HAVING A RETRACTABLE ROLLER

CROSS-REFERENCES TO RELATED APPLICATIONS

This is a division of application Ser. No. 09/834,874 filed Apr. 13, 2001, now U.S. Pat. No. 6,743,204, which is incorporated herein in its entirety. The following applications are related to the present application: "Spring Loaded Implantable Drug Infusion Device", assigned application Ser. No. 09/561,583, now U.S. Pat. No. 6,645,176; and "Implantable Drug Delivery Device with Peristaltic Pump Having A Biased Roller," assigned application Ser. No. 09/835,208, filed Apr. 13, 2001.

FIELD OF THE INVENTION

The present invention relates to an implantable drug delivery device for infusing a therapeutic agent into an organism, and more particularly, relates to a drug delivery device with a peristaltic implantable pump having an improved construction for installation of a drug delivery tube to the pump.

BACKGROUND OF THE INVENTION

Implantable drug infusion devices are well known in the art. These devices typically include a medication reservoir within a generally cylindrical housing. Some form of fluid flow control is also provided to control or regulate the flow of fluid medication from the reservoir to the outlet of the device for delivery of the medication to the desired location in a body, usually through a catheter. These devices are used to provide patients with a prolonged dosage or infusion of a drug or other therapeutic agent.

Active drug infusion devices feature a pump or a metering system to deliver the drug into the system of a patient. An example of such a drug infusion pump currently available is the Medtronic SynchroMed programmable pump. Additionally, U.S. Pat. No. 4,692,147 (Duggan), U.S. Pat. No. 5,840,069 (Robinson), and U.S. Pat. No. 6,036,459 (Robinson), assigned to Medtronic, Inc., Minneapolis, Minn., disclose body-implantable electronic drug administration devices comprising a peristaltic (roller) pump for metering a measured amount of drug in response to an electronic pulse generated by control circuitry associated within the device. Each of these patents is incorporated herein by reference in their entirety for all purposes. Such devices typically include a drug reservoir, a fill port, a peristaltic pump having a motor and a pumphead to pump out the drug from the reservoir, and a catheter port to transport the drug from the reservoir via the pump to a patient's anatomy. The drug reservoir, fill port, peristaltic pump, and catheter port are generally held in a housing, or bulkhead. The bulkhead typically has a series of passages extending from the drug reservoir and through the peristaltic pump that lead to the catheter port, which is typically located on the side of the housing. The peristaltic pump comprises a pumphead having rollers, a race or cavity defined by the bulkhead, and a pump tube that is threaded or inserted between the rollers and the race. The peristaltic pumps use the rollers to move a drug through the pump tube from the drug reservoir to the catheter port. The drug is then pushed by the pump through a catheter connected to the catheter port, and is delivered to a targeted patient site from a distal end of the catheter.

In the assembly or fabrication of peristaltic pumps, the pump tube must be installed in the device. More specifically, the pump tube must be threaded or inserted between the pump rollers and a race, and this installation is typically done as the pumphead is rotated. In conventional peristaltic pumps, the pump rollers can impede the installation of the pump tube between the rollers and the race. Impeding the insertion of the pump tube between the rollers and the race can increase manufacturing costs, and decrease ease and flexibility of manufacturing, as well as give rise to the potential for excessive load and/or damage to the pump tube during installation between the rollers and the race. It is an object of the present invention to provide an implantable drug infusion device which reduces or eliminates some or all of the difficulties in conventional devices and their manufacture.

It is an object of the present invention to provide an implantable drug infusion device which reduces or wholly overcomes some or all of the difficulties inherent in prior known devices. Particular objects and advantages of the invention will be apparent to those skilled in the art, that is, those who are knowledgeable or experienced in this field of technology, in view of the following disclosure of the invention and detailed description of preferred embodiments.

SUMMARY OF THE INVENTION

The present invention provides an implantable drug infusion or delivery device which features a peristaltic pump having a new configuration, incorporating at least one retracting roller to provide for easier installation of the pump tube between the roller and the race during manufacture of the device.

In accordance with one aspect, an implantable drug infusion device includes a bulkhead having a race. A pump tube having an inlet and an outlet is positioned within the race, the race configured to support the tube along a path. A roller assembly is configured to compress the tube against the race at one or more points along the path, and the roller assembly includes a hub and at least one roller biased against the pump tube. A drive assembly drives the roller assembly relative to the pump tube along the path so as to move a liquid through the pump tube. The roller assembly has at least one retracting roller operably connected to the hub and/or to at least one adjacent roller to permit retraction of the roller during installation of the pump tube between the roller and the race.

In accordance with another aspect, the roller assembly includes at least one retracting roller operably connected to a retracting roller arm or roller housing. The roller assembly is designed so that the retracting roller can be retracted during fabrication of the device. In a preferred embodiment, the roller assembly includes at least one biasing member or spring operably connected to the retracting roller to bias the roller against the pump tube after installation of the pump tube between the roller and the race. Further, the biasing member can be compressed when the retracting roller arm is retracted from the race so that the space between the roller and the race is increased to provide for reduced impedance of travel of the pump tube between the roller and the race. Reduced impedance to travel of the pump tube is particularly desirable during the threading or insertion of the pump tube between the roller and the race during device manufacture. Still further, the retracting roller can be returned to or substantially close to its initial position prior to retraction and installation of the pump tube between the roller and the race.

In a preferred embodiment of the invention, the biasing member, such as a spring, is operably applied to at least one retracting roller arm or roller of the peristaltic pump. In another preferred embodiment, the peristaltic pump has more than one retracting roller and corresponding retracting roller arm or roller housing and biasing member operably connected thereto.

In accordance with yet another aspect, an implantable drug infusion device includes a bulkhead having a race, a first chamber, and a second chamber. A pump tube has an inlet and an outlet and is positioned within the race. A motor assembly is positioned within the first chamber, a pumphead assembly is positioned within the second chamber, and the motor assembly drives the pumphead assembly. The pumphead assembly includes a roller assembly having a hub (or base) and three retracting roller arms. Each retracting roller arm has a roller and is pivotally connected to the hub. A drive assembly drives the roller assembly relative to the tube along the path so the rollers compress the tube to move a liquid through the tube. A biasing member or spring is operably connected to each retracting roller arm, which can be compressed to an amount sufficient to retract the roller arm as may be desired during installation of the pump tube between the roller and the race. Further, the spring can bias the corresponding roller against the pump tube during normal operation of the device.

From the foregoing disclosure, it will be readily apparent to those skilled in the art, that is, those who are knowledgeable or experienced in this area of technology, that the present invention provides a significant advance over the prior art. The present invention will further allow for less stringent manufacturing tolerances, increased manufacturing flexibility, reduction and/or elimination of excessive load and/or damage to the pump tube during installation, and improved performance. These and additional features and advantages of the invention disclosed herein will be further understood from the following detailed disclosure of preferred embodiments.

BRIEF DESCRIPTION OF THE DRAWINGS

Preferred embodiments are described in detail below with reference to the appended drawings.

The accompanying drawings, which are incorporated into and form a part of this specification, together with the description, serve to explain the principles of the invention. The drawings are not drawn necessarily to scale, are only for the purpose of illustrating a preferred embodiment of the invention, and are not to be construed as limiting the invention. Some features of the implantable drug delivery device depicted in the drawings have been enlarged or distorted relative to others to facilitate explanation and understanding. The above mentioned and other advantages and features of the invention will become apparent upon reading the following detailed description and referring to the accompanying drawings in which like numbers refer to like parts throughout and in which:

FIG. 15 is section view, taken along lines 15-15 of FIG. 14.

DESCRIPTION OF THE PREFERRED EMBODIMENTS

Figure 1:
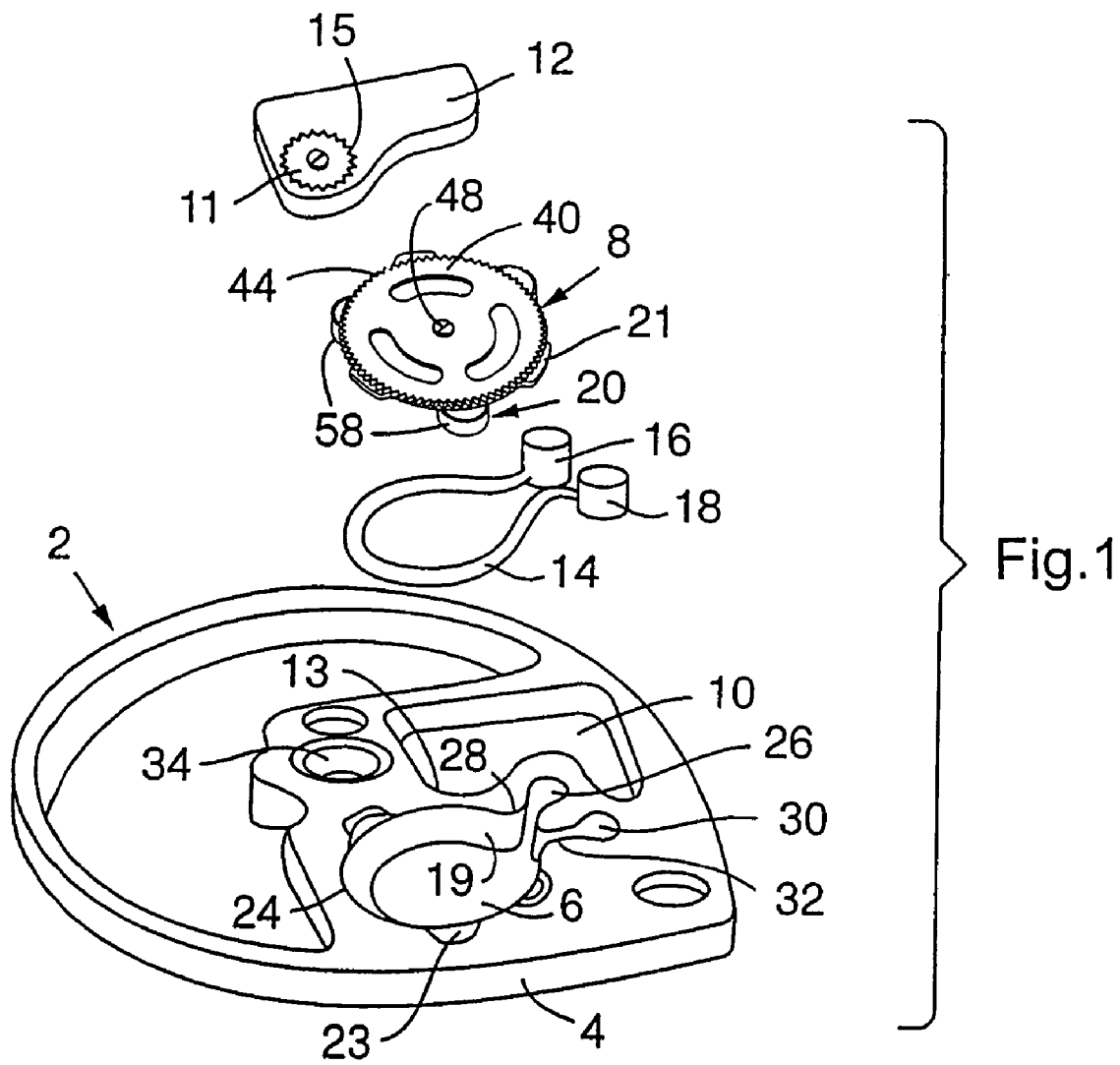
FIG. 1 is an exploded perspective view of an implantable drug delivery device in accordance with the present invention.

As shown in FIG. 1, an implantable drug delivery device 2 in accordance with the invention comprises a bulkhead 4 containing a number of chambers and cavities sized and configured to house various subsystems of the implantable drug infusion device. In particular, bulkhead 4 has a first chamber 6 sized and configured to house a peristaltic pumphead assembly 8. A second chamber 10, sized and configured to house a motor assembly 12 which drives pumphead assembly 8, is positioned adjacent first chamber 6 and separated therefrom by a wall 13. Other chambers of bulkhead 4 house a battery and the electronic circuitry (not shown) used to operate implantable drug infusion device 2 and to control the dosage rate of the medication into the body.

Pumphead assembly 8 includes a compression member, such as roller arm assembly 20, for compressing a pump tube 14 having an inlet 16 and an outlet 18. First chamber 6 has a generally circular wall 24 defining a pump race 19. Pump tube 14 is placed in first chamber 6 in close proximity to wall 24 so that roller arm assembly 20 may force the tube against the wall, thereby forcing medication to move through the tube in a known peristaltic manner. Flanges 21 extending outwardly from pumphead assembly 8 are received in recesses 23 formed in first chamber 6, supporting pumphead assembly 8 in first chamber 6. Inlet 16 is placed in a pump inlet cavity 26 formed in bulkhead 4. Pump inlet cavity 26 is connected to the pump race 19 by a pump inlet race ramp 28. Pump tube outlet 18 is placed in a pump outlet cavity 30 formed in bulkhead 4. Pump tube outlet cavity 30 is connected to the pump race 19 by a pump outlet race ramp 32. In a preferred embodiment, both pump inlet race ramp 28 and pump outlet race ramp 32 have an arcuate geometry. A cover (not shown) is also provided for bulkhead 4 to provide protection for the components of drug infusion device 2. Motor assembly 12 includes a motor (not shown) which drives a four-stage gear assembly 11, only the fourth stage of which is visible. Teeth 15 are formed on the periphery of the fourth stage of gear assembly 11.

Bulkhead 4 has an integral fill port cavity 34, sized and configured to house a septum and components to retain the septum. Drugs are injected through the septum to fill a reservoir (not shown) contained within a lower portion of bulkhead 4. A pathway is formed between the reservoir and pump inlet cavity 26, through which drugs are introduced into pump tube 14. The drugs exit pump outlet cavity 30 and travel through another pathway formed in bulkhead 4 to a catheter port on the periphery of bulkhead 4 from which the drug exits the device 2 and enters the anatomy of the individual. The structure of the septum, retaining components, pathways, and catheter port are known to one of skill in the art and are not shown here.

Figure 2:
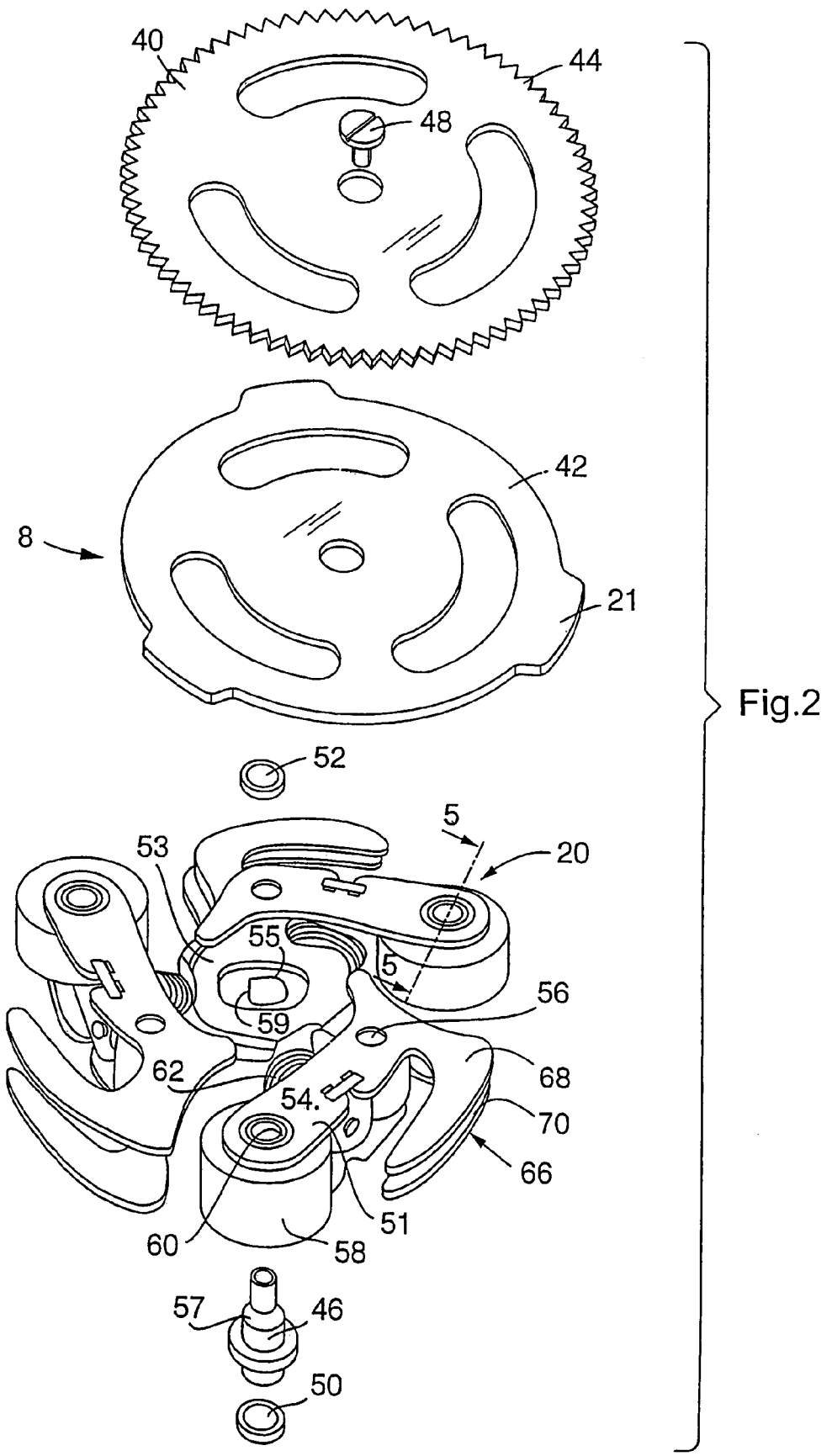
FIG. 2 is an exploded perspective view of a pumphead assembly of the implantable device of FIG. 1.

Referring now to FIG. 2, pumphead assembly 8 is shown in exploded form. Pumphead assembly 8 includes a drive gear 40 with teeth 44 formed about its periphery. A support plate 42 is positioned below drive gear 40. Flanges 21 extend outwardly from support plate 42 and, as described above, are received in recesses 23 of bulkhead 4, and preferably welded thereto. Roller arm assembly 20 is positioned below support plate 42. Drive shaft 46 extends axially through apertures in roller arm assembly 20, support plate 42, and drive gear 40, and is retained by retaining screw 48. Drive shaft 46 is supported for rotation at its lower end by lower bearing 50, and at a central location, between roller arm assembly 20 and support plate 42, by upper bearing 52.

Roller arm assembly 20 comprises a central hub 53 having an aperture 55 through which drive shaft 46 extends. Flat 57 on drive shaft 46 mates with flat 59 of aperture 55 such that roller arm assembly 20 rotates as drive shaft 46 rotates. A plurality of retracting roller arms 54 are each pivotally secured by a pin 56 to hub 53. Each retracting roller arm 54 comprises upper plate 51 and lower plate 61. A roller 58 is pivotally secured to each roller arm 54 by an axle 60. As seen in FIG. 2, axle 60 extends between upper plates 51 and corresponding lower plates 61. Axle 60 passes through an inner race (not shown) of roller 58. In the illustrated embodiment, roller arm assembly 20 is shown with three roller arms 54 and three corresponding rollers 58, however, the number of roller arms 54 and rollers 58 may be greater or lesser than three.

Figure 3:
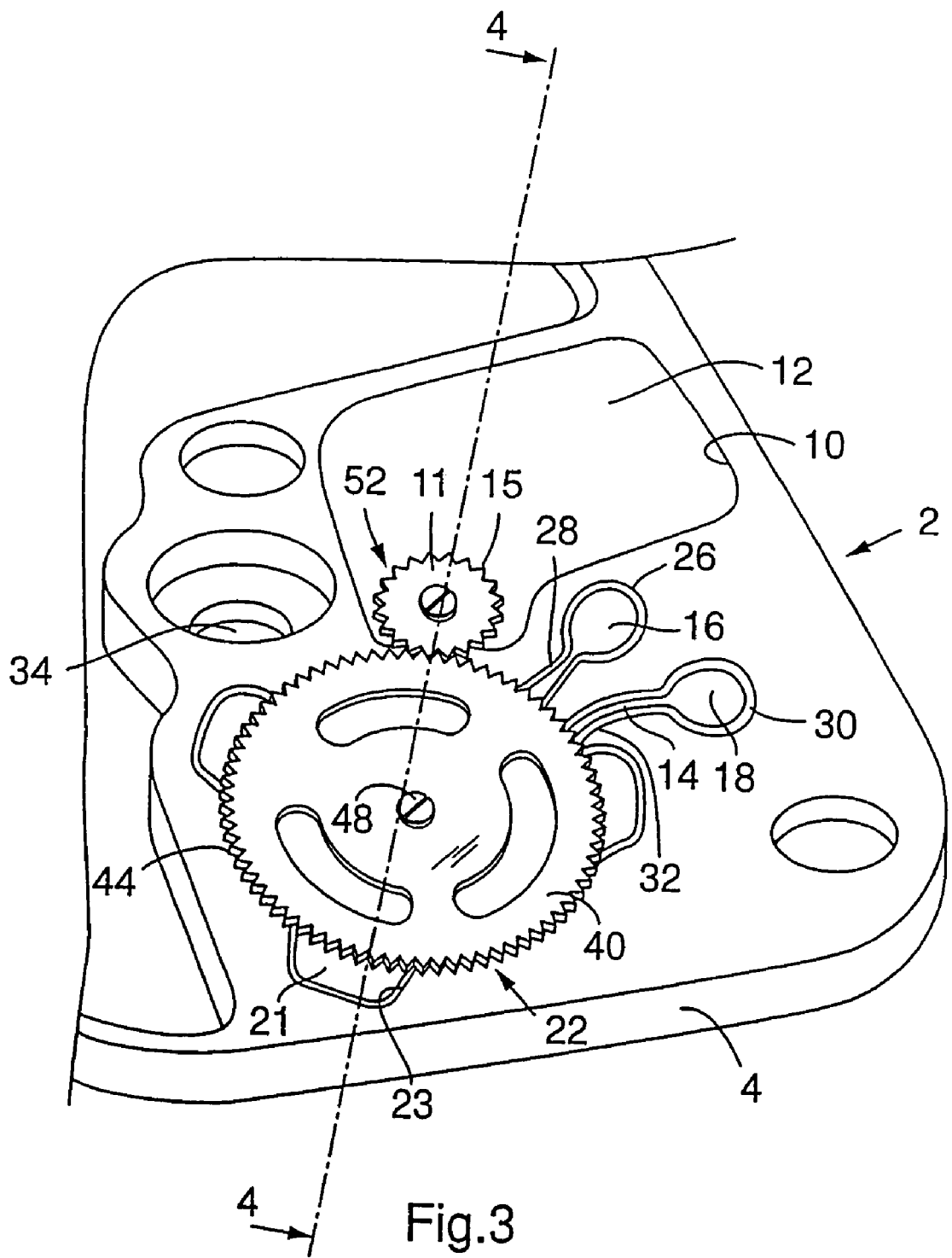
FIG. 3 is perspective view, partially cut away, of the implantable device of FIG. 1 shown in its assembled state.
Figure 4:
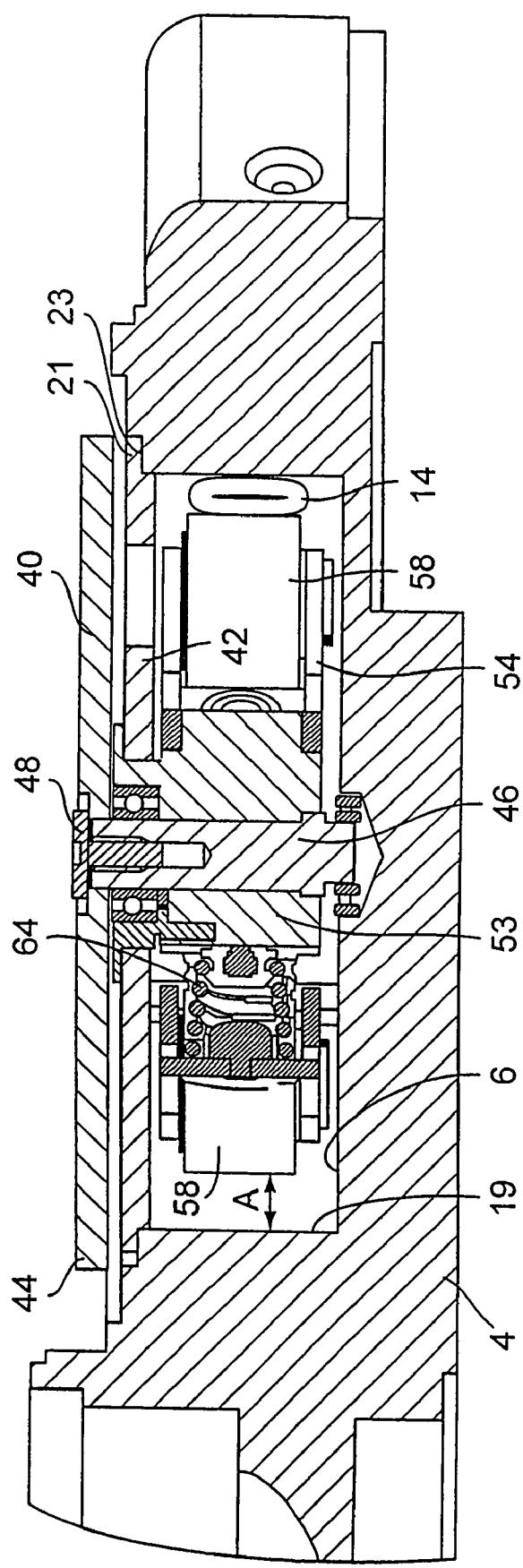
FIG. 4 is a section view, taken along lines 4-4 of FIG. 3, of the implantable device of FIG. 1.
Figure 5:
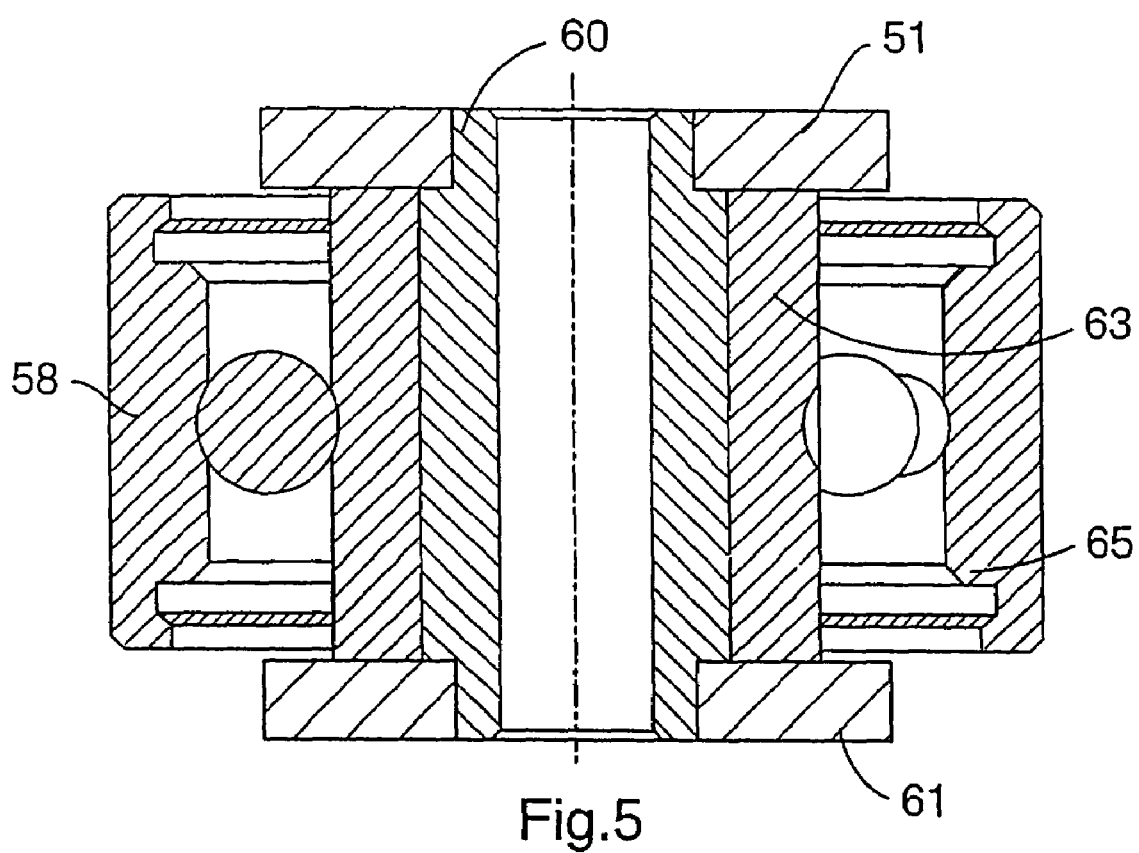
FIG. 5 is a section view, taken along lines 5-5 of FIG. 2, of a retracting roller arm of the implantable device of FIG. 1.

As seen in FIGS. 3 and 4, teeth 15 of gear assembly 11 drivingly engage teeth 44 of drive gear 40, thereby causing rollers 58 to move about race 19, compressing and occluding tube 14 as they move and forcing the drug therethrough in known peristaltic fashion. As noted above, inlet race ramp 28 and outlet race ramp 32 each have an arcuate geometry, which reduces the torque required as each roller 58 engages pump tube 14 during rotation of roller arm assembly 20.

Figure 6:
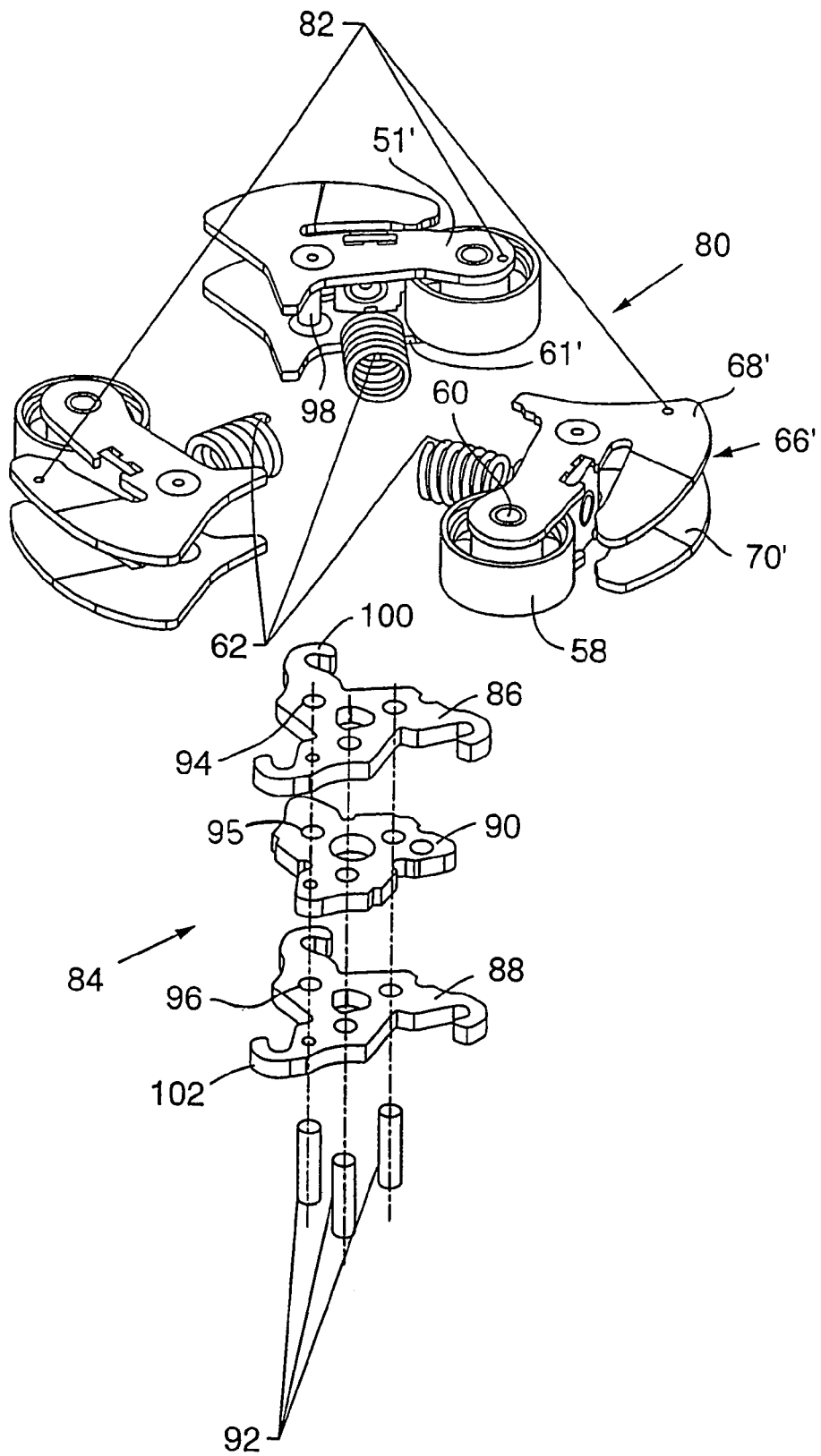
FIG. 6 is an exploded perspective view of an alternative embodiment of the roller arm assembly of FIG. 1.

Another embodiment of a roller arm assembly 80 is shown in FIG. 6. Roller arm assembly 80 comprises three retracting roller arms 82 pivotally secured to a hub 84. Hub 84 comprises upper plate 86, lower plate 88, and center plate 90. Rods 92 extend through apertures 94,95 and 96 formed in upper plate 86, center plate 90, and lower plate 88, respectively. Pivot pins 98 extend between upper plate 51' and lower plate 61' of each retracting roller arm 82. Hooks 100, 102 formed on upper plate 86 and lower plate 88, respectively, of hub 84, capture pivot pins 98. The force of springs 62 acting on retracting roller arms 82 helps maintain retracting roller arms 82 in position on hub 84.

Referring to FIGS. 2, 4, 7A, 7B, 7C, 8A and 8B, each retracting roller arm 54 and its corresponding roller 58 can be temporarily retracted away from race 19 and towards hub 53 by movement about pin 56 so that pump tube 14 can be inserted between roller 58 and race 19. The retraction of roller 58 away from race 19 can be accomplished in a number of ways. For example, a force 300 can be exerted on roller 58 and/or roller arm 54 to push them in towards hub 53 by hand and/or using an appropriate tool (not shown). Retraction of retracting roller arm 82 and corresponding roller 58 shown in FIG. 6 can be similarly accomplished.

Alternatively, a tool 200 having a least one wire 201 can be inserted into hole 202 defined in the center of roller axle 60, towards hub 53. As shown in FIG. 8B, tool 200 has a sliding disk 203 that moves substantially perpendicular relative to roller arm 54. As the disk is moved towards the roller arms 54 the wires 201 move radially inward, thereby retracting the rollers 58. After wires 201 are inserted into respective holes 202 defined in axles 60, sliding disk 203 can be moved away from center end 205, and thus move the wires 201, which in turn retract the rollers 58. More specifically, as sliding disk 203 is moved away from center end 205, sliding disk 203 exerts a force that moves wires 201 towards each other and hub 53 (not shown in FIG. 8B), thereby retracting rollers 58 towards hub 53 and away from race 19. Retraction of retracting roller arm 82 and corresponding roller 58 shown in FIG. 6 can be similarly accomplished.

Figure 7A:
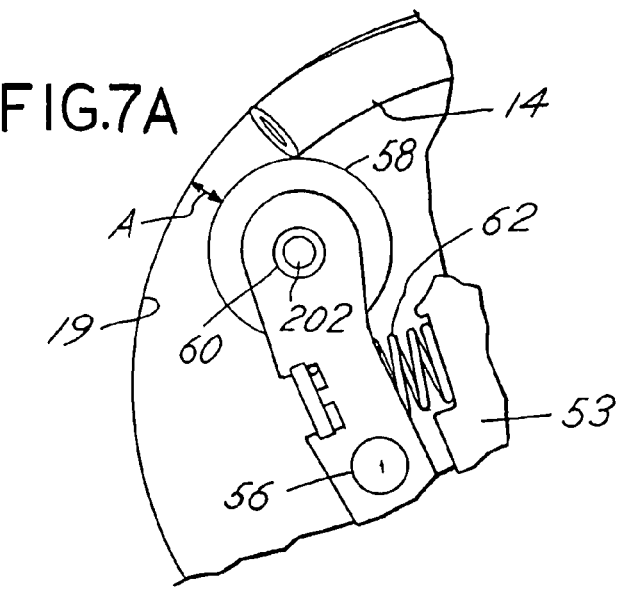
FIGS. 7A, 7B, and 7C are partially cut away top views that illustrate the retraction of a roller arm and roller for the installation of a pump tube between the roller and a race.
Figure 7B:
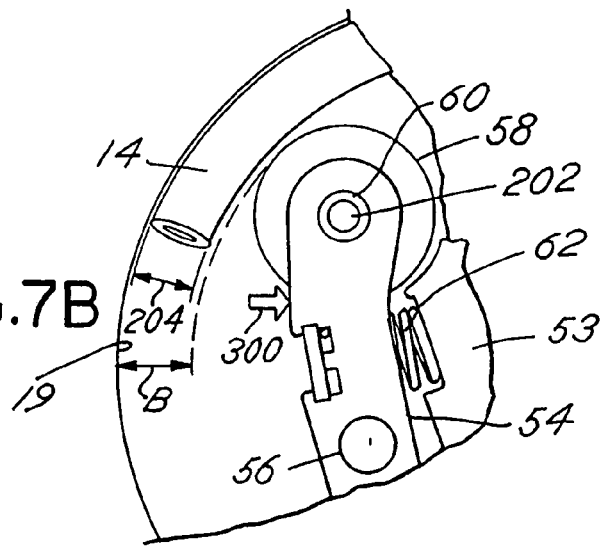
Figure 7C:
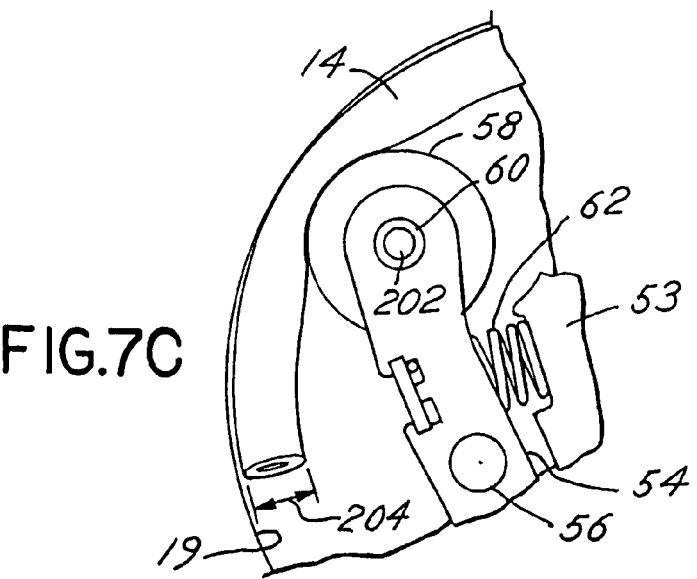

The retracting movement of roller 58 will increase the gap A defined by roller 58 and race 19 as shown in FIG. 7A to gap B as shown in FIG. 7B. The gap defined by roller 58 and race 19 can be thus increased so that it is larger than the outside diameter 204 of pump tube 14. However, it is not necessary for the retraction to be that large. The retraction need only be large enough to make insertion of pump tube 14 easier than without retraction, and so that pump tube 14 can be easily threaded or inserted between roller 58 and race 19. FIG. 7A illustrates roller 58 relative to race 19 prior to retraction. FIG. 7B illustrates roller 58 relative to race 19 upon retraction to permit easy installation of pump tube 14, and wherein spring 62 is compressed beyond its normal operating state prior to installation of pump tube 14. FIG. 7C illustrates roller 58 relative to race 19 after retraction and installation of pump tube 14, and after roller 58 is moved to or substantially close to its pre-retraction position relative to race 19, and wherein spring 62 is in a less-compressed state than during roller retraction. Thus, after installation of pump tube 14 between roller 58 and race 19, biasing member or spring 62 places a load force on the pump tube 14 to provide occlusion to the tube to move a drug along the tube during operation of the device 2. As shown in FIG. 7C, spring 62 is thus somewhat compressed to maintain a load on pump tube 14 after installation of pump tube 14.

The movement of roller 58 to or substantially close to its pre-retracted position relative to race 19 can be easily accomplished by reversing or removing force 300 that had been exerted to retract roller 58 away from race 19. Further, spring 62 can also function as a biasing member to ensure that roller 58 is returned to close to its pre-retracted position relative to race 19 after installation of pump tube 14. Still further, spring 62 can ensure that roller 58 is biased against pump tube 14 during operation of device 2.

Figure 8A:
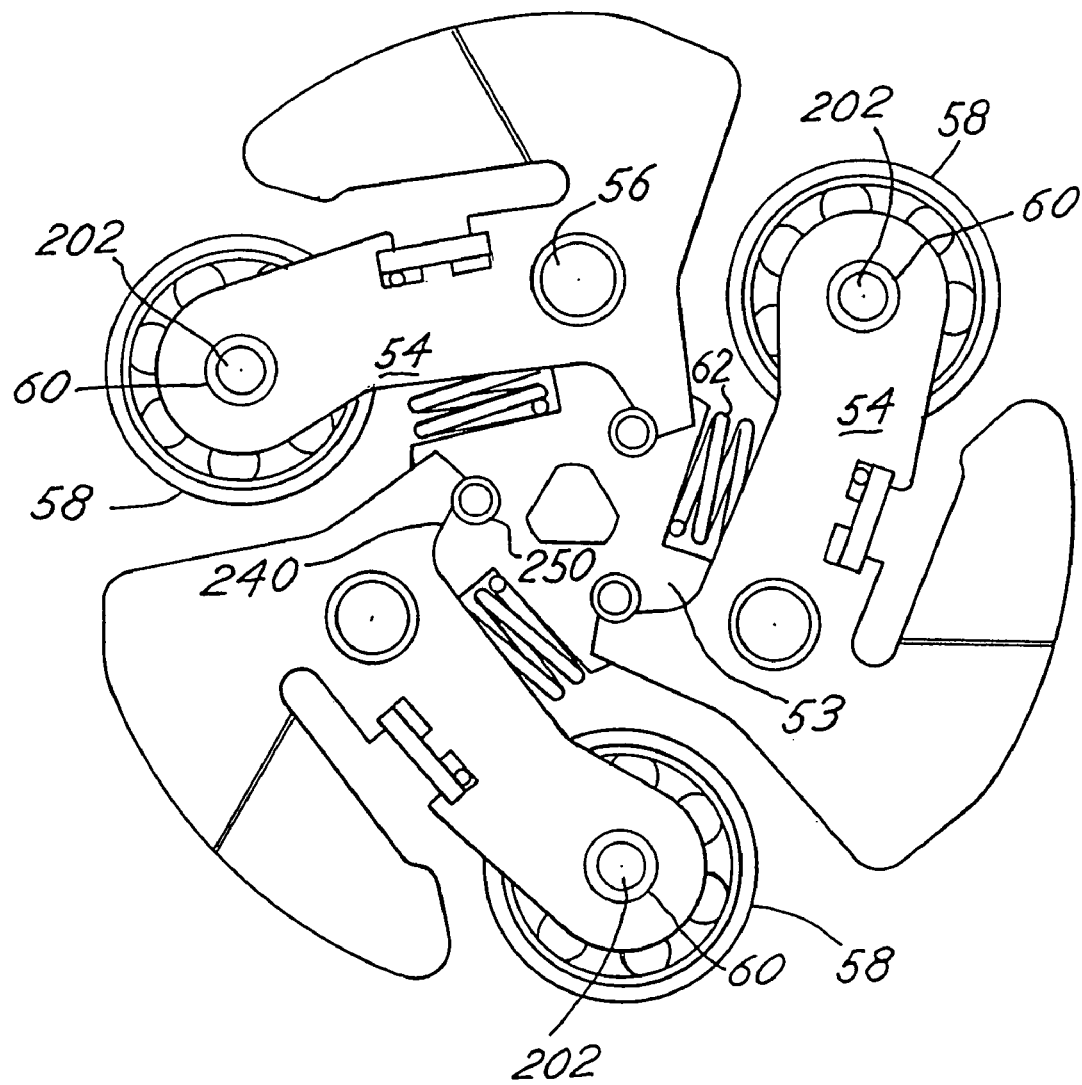
FIG. 8A is a top view of an embodiment of the present invention, wherein each roller arm has an opening for receipt of a tool to accomplish retraction of each roller arm and a corresponding roller.
Figure 8B:
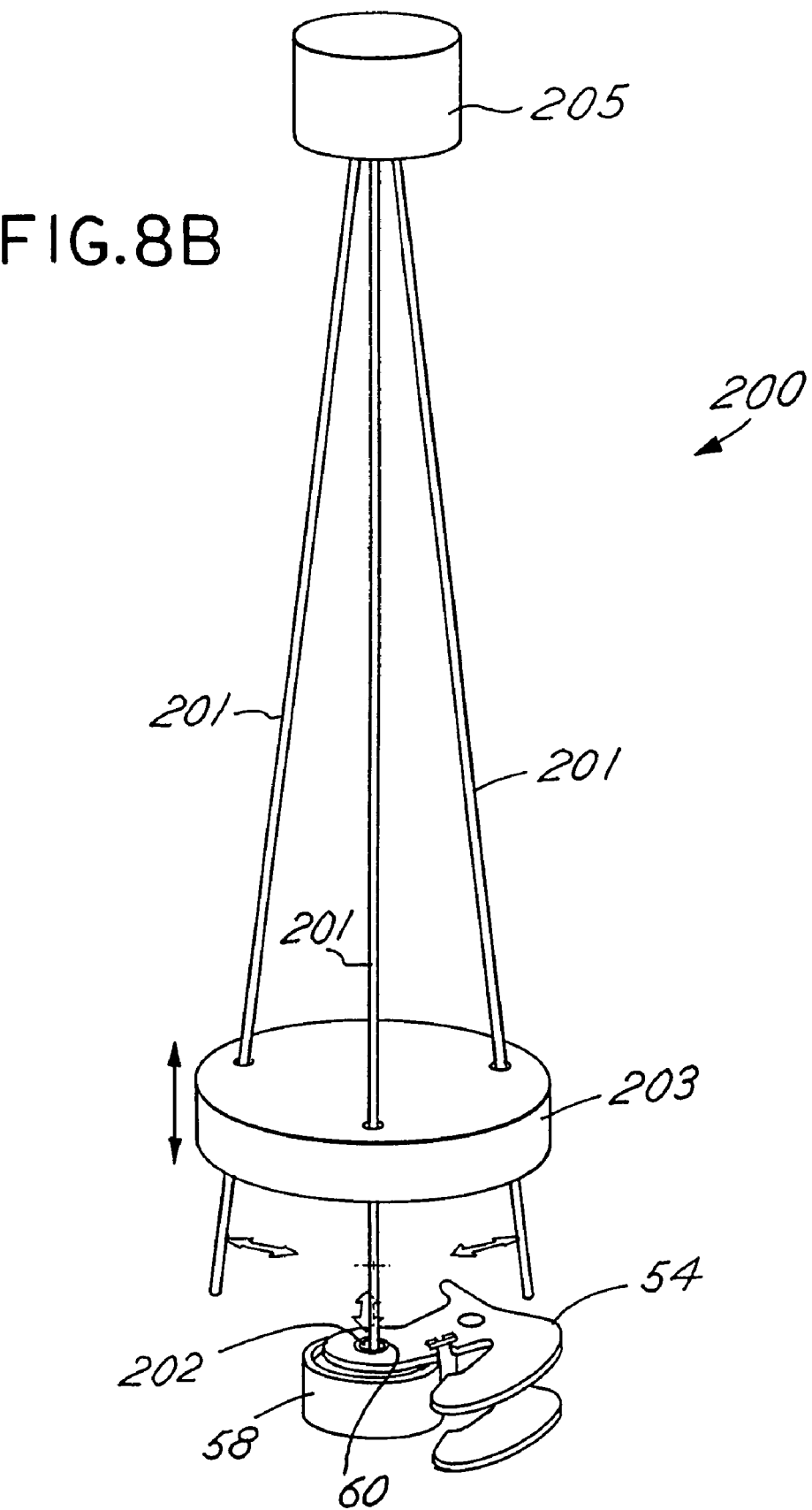
FIG. 8B is a perspective view of a tool for retraction and a roller arm and a corresponding roller.

As shown in FIG. 8A, roller arms 54 can have a flange 240 that contacts a stop pin 250, thereby stopping movement of roller arm 54 at a certain point as may be desired.

Figure 9:
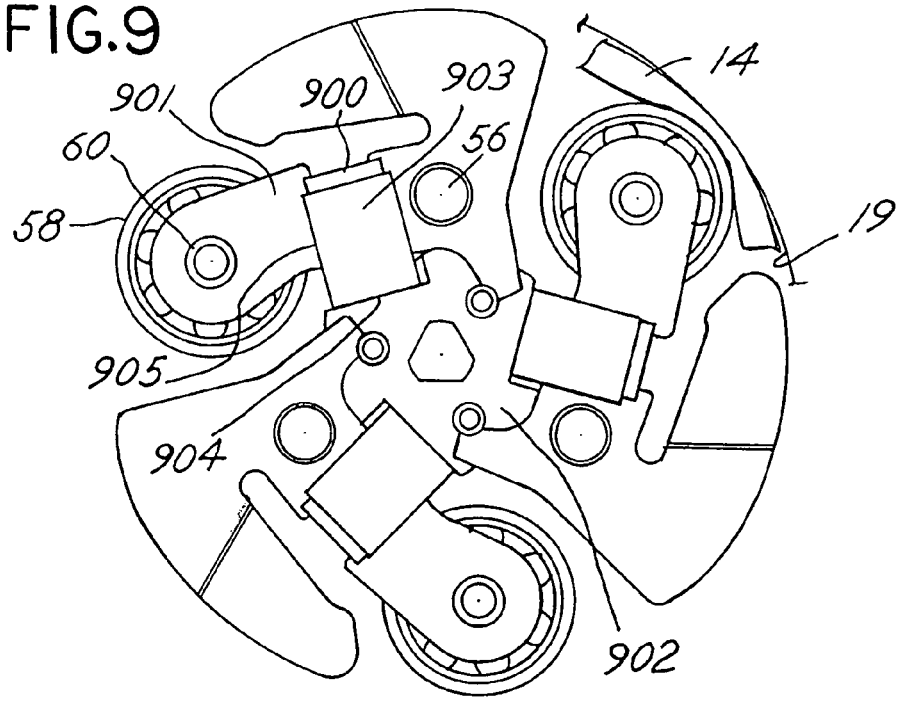
FIG. 9 is a top view of another embodiment of the present invention, wherein a spacer is inserted after roller retraction and installation of the pump tube between the rollers and the race. After installation of the pump tube, the spacer forces the roller against the tube to provide occlusion.

FIG. 9 shows an alternative embodiment of the present invention, having a spacer 903 that can be positioned between axle 60 and pin 56. For installation of a pump tube 14, spacer 903 is not present, allowing roller arm 901 to be retracted towards hub 902. After installation of pump tube 14 between roller 58 and race 19, spacer 903 can be inserted into space 905 defined by roller arm 901 and hub 902. Spacer 903 can be rigid or flexible and be made of any suitable material, such as metal, plastic, or an elastomer. Rollers 58 thus can be retracted and moved radially inward towards hub 902 for installation of pump tube 14, rollers 58 can then be moved back against the installed pump tube 14, and spacer 903 can then be inserted into space 905 so that roller 58 can be in position to place an operational load to occlude pump tube 14 during operation of device 2. As further shown in FIG. 9, spacer 903 can be placed between a first platform 900 of roller arm 901 and a second platform 904 of hub 903 so that roller 58 will be in position to place an operational load on installed pump tube 14.

Figure 10:
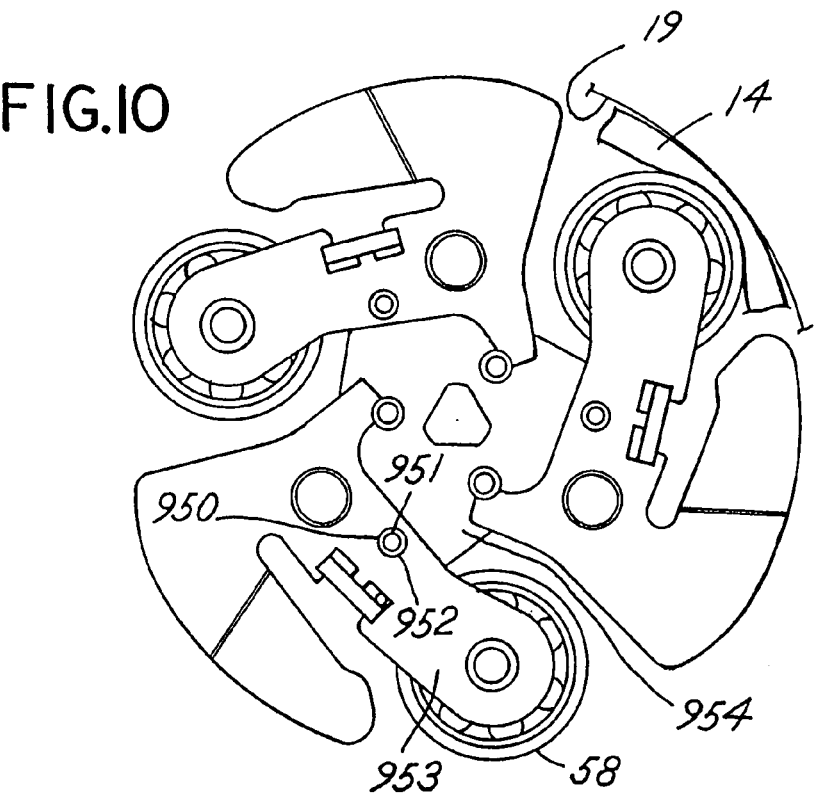
FIG. 10 shows another embodiment of the present invention wherein a pin is inserted into a hole in a roller arm after roller retraction and installation of a pump tube between the roller and the race. After installation of the pump tube, the pin keeps the roller against the tube to provide occlusion.

FIG. 10 shows another alternative embodiment of the present invention. Roller arm 953 can be retracted away from race 19 to permit easy installation of pump tube 14 between roller 58 and race 19. Retracting arm 953 can then be moved back against the installed pump tube 14 until it is locked into position by lock 950. Lock 950 comprises a pin 951 and hole 952 defined by roller arm 953. Lock 950 locks roller arm 953 to hub 954 when pin 951 is inserted into hole 952. Pin 951 can be spring loaded if desired. Those skilled in the art will recognize that lock 950 can alternatively comprise detent designs, including balls and/or snaps. Pin 951 can be removed from hole 952 so that roller arm 953 and roller 58 can be retracted and radially moved inward towards hub 954. After installation of pump tube 14 between rollers 58 and race 19, the roller arm 953 can be radially moved outward away from hub 954, and pin 951 can be inserted into hole 952, thereby placing roller 58 into operational position to occlude pump tube 14 as desired.

Referring back to FIG. 2, each retracting roller arm 54 and its corresponding roller 58 is adjustably biased outwardly by biasing member, such as a spring 62. In a preferred embodiment, spring 62 is a coil spring. In a preferred embodiment, spring 62 is made of a highly corrosion and fatigue resistant alloy. Suitable materials include cobalt alloys and/or stainless steel. In other preferred embodiments, a nitinol shape memory alloy may be used for spring 62.

The retracting roller of the present invention provides additional advantages over the prior art devices. In accordance with the present invention, the pump tube is easier to install between the rollers and the race than in the manufacture of prior art devices. In addition, the potential for excessive load or damage to the pump tube during installation is reduced and/or eliminated.

In an alternative embodiment, retracting rollers 404 can be retracted by compressing a combination of biasing members or springs 402 operably connected to the roller. FIGS. 11 through 15 show such an embodiment, which can be referred to as a retracting bobbin embodiment. In this embodiment, a roller assembly 500 is assembled and can replace roller arm assembly 20 in FIG. 2. Thus, roller assembly 500 is configured to compress a pump tube 14 against the race 19 at one or more points along a path. Roller assembly 500 comprises at least one roller 404, and at least two biasing members or springs 402 operably connected to the roller 404 to adjustably bias the roller 404 against a pump tube 14. The two biasing members 402 form an angle 501. Further, roller housings 400 are connected to at least one adjacent roller housing 400 by a spring 402. This embodiment permits rollers 404 to be retracted if desired to install a pump tube 14 by compressing springs 402. More specifically, the retracting movement of rollers 404 will increase gap A defined by rollers 404 and race 19 similar to that shown in FIGS. 7A through 7C.

As illustrated in FIGS. 11 through 15, rollers 404 are positioned within a corresponding roller housing 400. In this embodiment, rollers 404, roller pins 405, roller housings 400 and springs 402 are positioned between a lower plate 406 and an upper plate 408. Lower plate 406 and upper plate 408 define openings 409 to receive portions 410 and 412 of roller housings 400, respectively. Portions 410 and 412 of roller housings 400 are positioned within openings 409 and are nearly flush with bottom surface 414 of bottom plate 406, and top surface 416 of upper plate 408, respectively. Roller pins 405 can be pressed or staked into roller housing 400, with spacers 407 providing a gap between roller 404 and roller housing 400.

Figure 11:
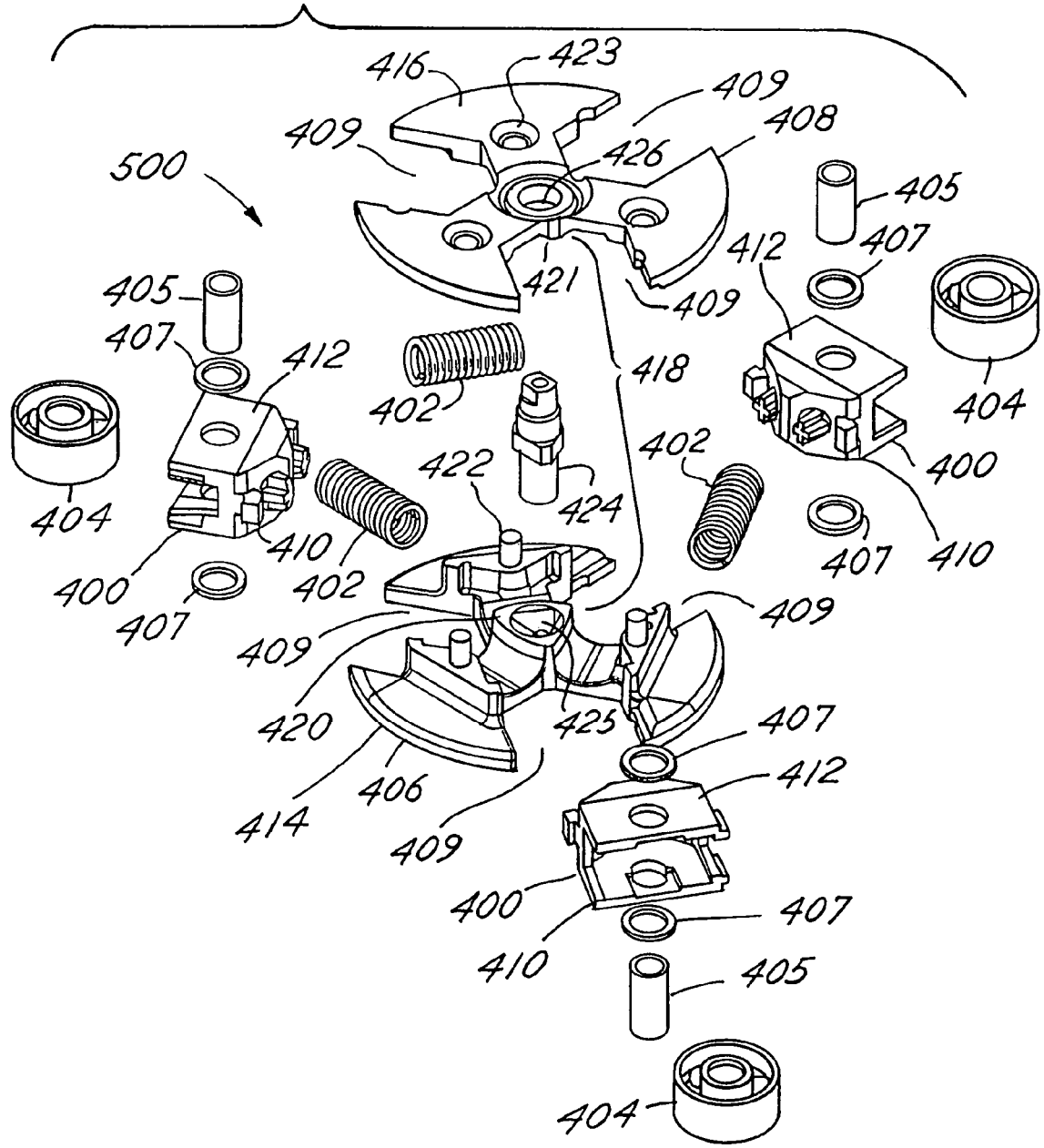
FIG. 11 is an exploded perspective view of an alternative embodiment, sometimes referred to herein as the bobbin embodiment, to the roller arm assembly 20 shown in FIG. 2.
Figure 12:
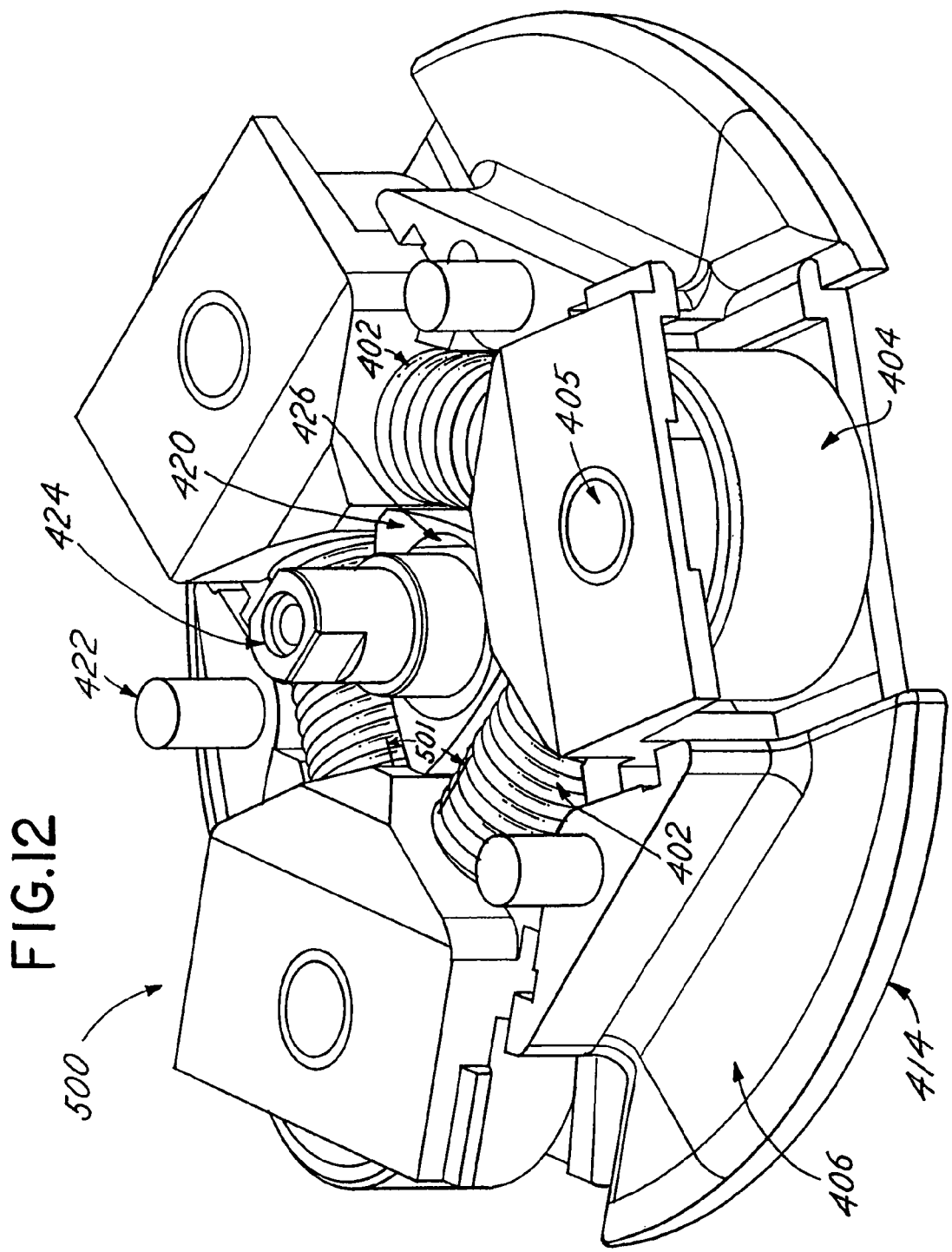
FIG. 12 is a perspective view of the bobbin embodiment shown in FIG. 11 as assembled, without an upper plate shown.
Figure 13:
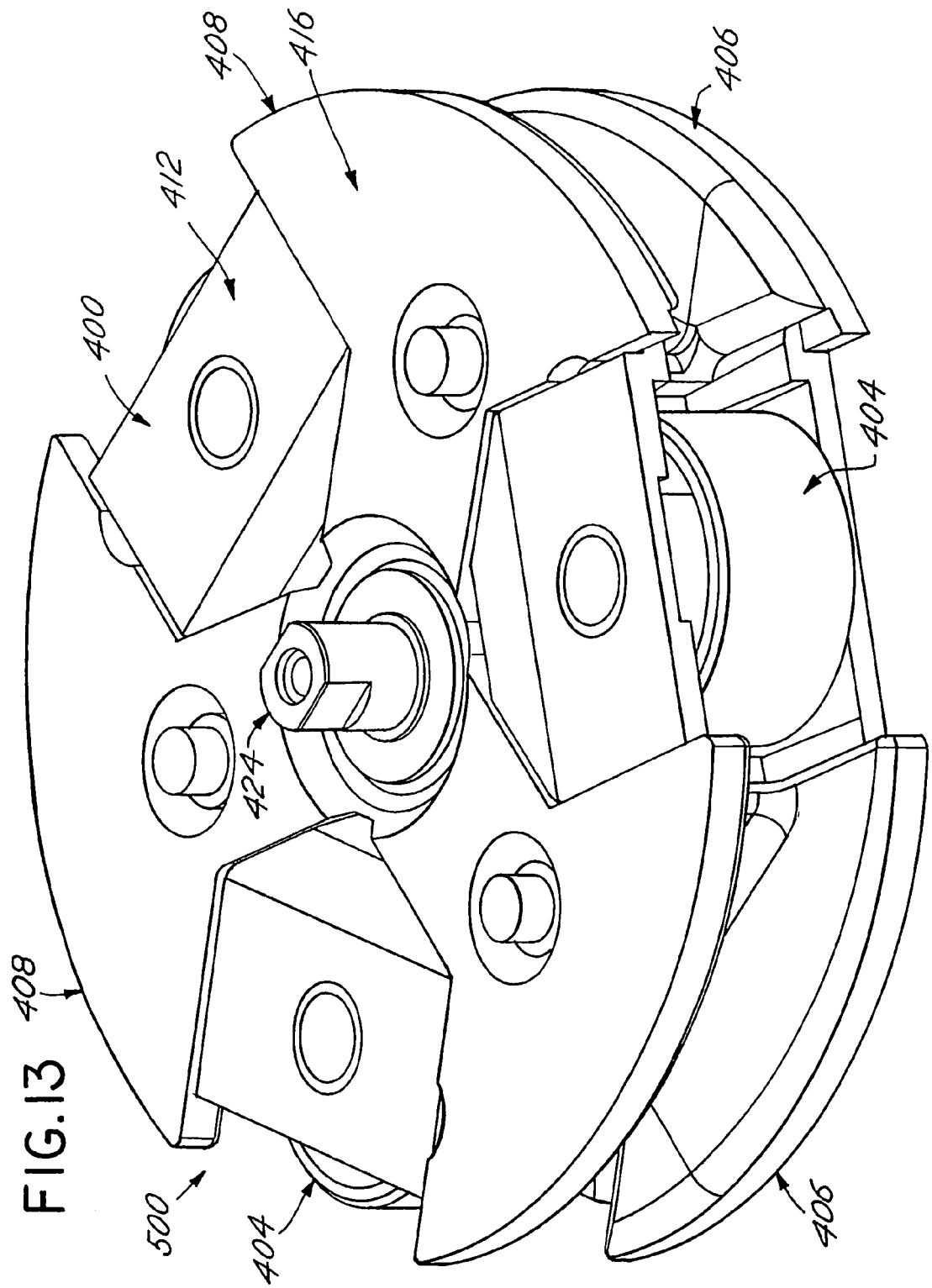
FIG. 13 is a perspective view of the bobbin embodiment of the present invention shown in FIG. 12, illustrating the attachment of an upper plate.
Figure 14:
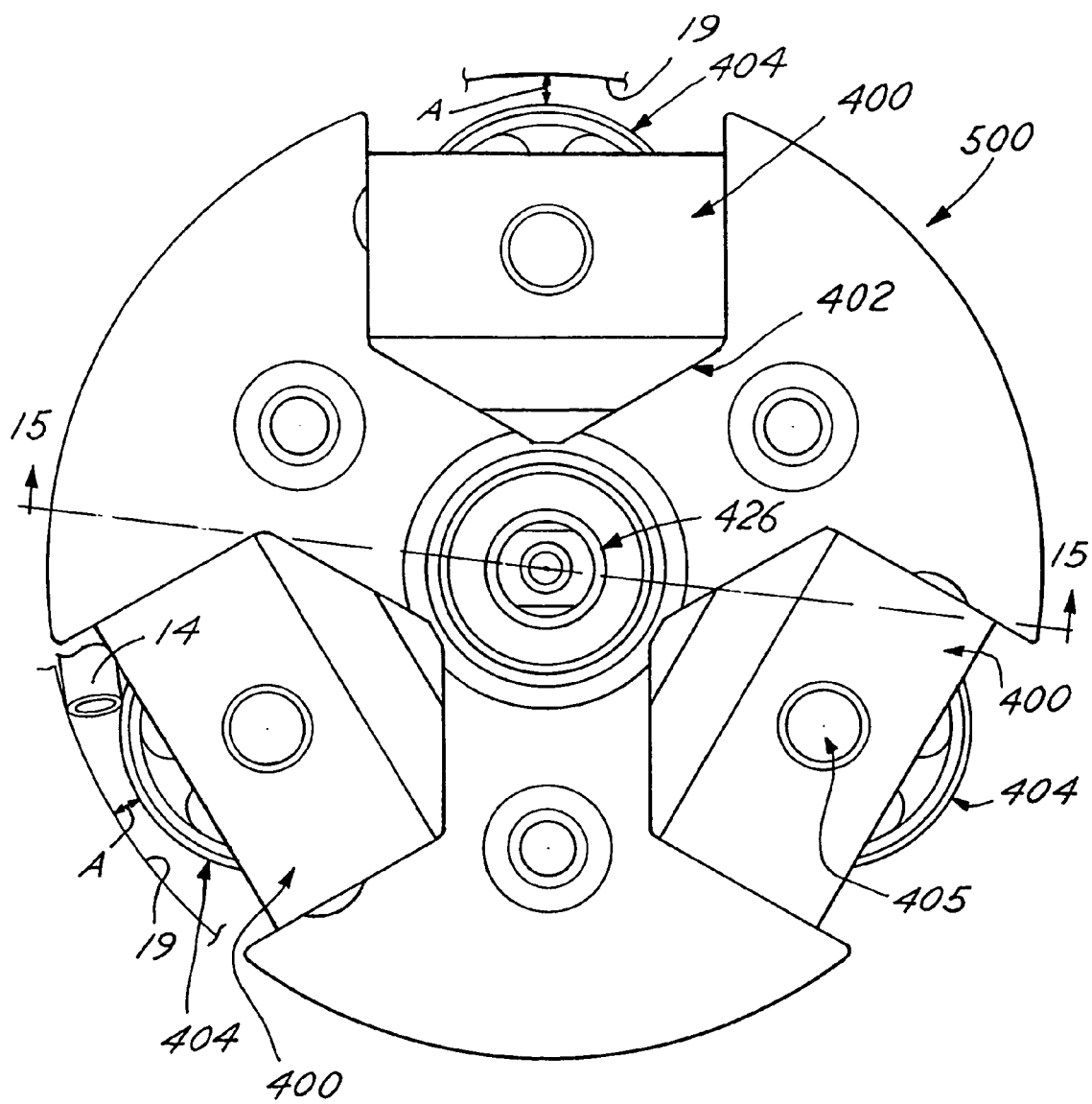
FIG. 14 is a top view of the bobbin embodiment illustrated in FIG. 13.

Hub 418 is comprised of portion 420 of bottom plate 406 and portion 421 of upper plate 408. Portions 420 and 421 can mate with each other via mating member 422 of bottom plate 406 and a corresponding mating member 423 of upper plate 408. FIG. 11 shows each mating member 423 lined up and between the center of hub 418 and a corresponding roller pin 405 to form a straight line. Shaft 424 can be placed through hole 425 defined in bottom plate 406 and through hole 426 defined in top plate 408. Shaft 424 can be driven by a drive assembly (not shown) as described in the preceding embodiments.

Each roller housing 400 and its corresponding roller 404 is adjustably biased outwardly by a biasing member or spring 402. Roller housings 400 can also or alternatively be operably connected to hub 418, such as by springs similar to springs 402, including the springs 62 as shown in FIGS. 2, 4, 6, 7A, 7B, 7C, and 8A.

In a preferred embodiment, spring 402 is a coil spring. In a preferred embodiment, spring 402 is from a material selected from the group consisting of a cobalt, stainless steel or a nitinol shape memory alloy. It is to be appreciated that other retracting roller assembly constructions will be suitable, and are considered within the scope of the present invention. Suitable retracting roller assembly constructions will provide at least one retracting roller to permit easy installation of a pump tube between a roller(s) and a race, and after such installation, ensure that the roller, or other suitable compression member, is positioned against the pump tube. The positioning of the roller against the installed pump tube can be further accomplished by a biasing member to minimize the variation in load required to occlude the pump tube. Other suitable biasing members in addition to coil springs, include, for example, leaf springs and springs of other constructions, elastomeric members, closed or open cell elastomeric foam members, torsion bars, magnetic members, and solenoids.

In light of the foregoing disclosure of the invention and description of the preferred embodiments, those skilled in this area of technology will readily understand that various modifications and adaptations can be made without departing from the scope and spirit of the invention. All such modifications and adaptations are intended to be covered by the following claims.

What is claimed is:

1. A method of manufacture of an implantable drug infusion device comprising the steps of:
   (a) assembling a race configured to support a pump tube along a path;
   (b) assembling a roller assembly configured to apply pressure to the tube against the race at one or more points along the path, the roller assembly including at least one retracting roller;
   (c) inserting a part of a tool into a hole defined by an axle of the roller and moving the part of the tool away from the race;

(d) retracting the roller away from the race; and
(e) inserting a pump tube between the retracted roller and the race.

2. The method of manufacture of claim 1, wherein the step of assembling the roller assembly comprises assembling three or more retracting rollers, each retracting roller configured to apply pressure to the tube against the race, and the step of retracting comprises retracting each roller.

3. The method of manufacture of claim 2, wherein the step of retracting the roller away from the race comprises:
   inserting a first part of a tool into a first hole defined by an axle of a first roller;
   inserting a second part of the tool into a second hole defined by an axle of a second roller;
   inserting a third part of the tool into a third hole defined by an axle of a third roller; and
   moving the first, second, and third parts of the tool away from the race.

4. The method of manufacture of claim 3, wherein the step of retracting further comprises the step of sliding a sliding member along a length of the tool and toward the roller assembly, thereby causing the parts of the tool to move away from the race and towards each other.

5. The method of manufacture of claim 2, wherein the step of retracting further comprises:
   inserting a part of a tool into a corresponding hole defined by an axle of each roller; and
   moving each inserted part away from the race.

6. The method of manufacture of claim 5, wherein the step of retracting further comprises the step of sliding a sliding member along a length of the tool and toward the roller assembly, thereby causing the parts of the tool to move away from the race and towards each other.

7. The method of manufacture of claim 1, wherein the step of assembling the roller assembly comprises assembling two or more retracting rollers, each retracting roller configured to apply pressure to the tube against the race, and the step of retracting comprises retracting each roller.

8. The method of manufacture of claim 7, wherein the step of retracting the rollers away from the race comprises:
   inserting a first part of a tool into a first hole defined by an axle of a first roller;
   inserting a second part of the tool into a second hole defined by an axle of a second roller; and
   moving the first and second parts of the tool away from the race.

9. The method of manufacture of claim 8, wherein the step of retracting further comprises the step of sliding a sliding member along a length of the tool and toward the roller assembly, thereby causing the first and second parts of the tool to move away from the race and towards each other.

10. The method of manufacture of claim 1, wherein the step of retracting the roller away from the race further includes compressing a biasing member that biases the roller towards the race.

11. The method of manufacture of claim 10, further comprising the steps of:
    deretracting the roller by decompressing the biasing member; and
    allowing the roller to move towards the race so that the biasing member causes the roller to apply pressure to the tube.

12. The method of manufacture of claim 1, further having the step of assembling a drive assembly to drive the roller assembly relative to the pump tube along the path so as to move the liquid through the pump tube.

13. The method of manufacture of claim 1, further having the step of deretracting the roller by moving the roller towards the race, thereby allowing the roller to apply pressure to the tube against the race.

14. The method of manufacture of claim 1, wherein the step of retracting the roller away from the race further includes using a tool to retract the roller.

15. The method of manufacture of claim 1, wherein the step of assembling the race includes the step of assembling the race within a pumphead assembly.

16. The method of manufacture of claim 1, wherein the step of assembling the roller assembly includes the step of assembling the roller assembly within a pumphead assembly.

17. The method of manufacture of claim 1, wherein the step of assembling the race further includes the step of assembling the race within a housing.

18. The method of manufacture of claim 1, wherein the step of assembling the roller assembly includes the step of assembling the roller assembly within a housing.

* * * * *

UNITED STATES PATENT AND TRADEMARK OFFICE
CERTIFICATE OF CORRECTION

| | |
|---|---|
| PATENT NO. | : 7,434,312 B2 |
| APPLICATION NO. | : 10/826088 |
| DATED | : October 14, 2008 |
| INVENTOR(S) | : Christenson et al. |

It is certified that error appears in the above-identified patent and that said Letters Patent is hereby corrected as shown below:

Title Page, Inventor Names: "Mandred" should be deleted - should read --Manfred--; and Col. 10, Line 10, Claim 10: "biasesthe" should be deleted - should read --biases the--.

Signed and Sealed this

Twelfth Day of May, 2009

JOHN DOLL
*Acting Director of the United States Patent and Trademark Office*